(12) United States Patent
Riedel

(10) Patent No.: US 11,896,519 B2
(45) Date of Patent: Feb. 13, 2024

(54) ASSEMBLY FOR GLUTEAL CLEFT MOISTURE REDUCTION

(71) Applicant: David R Riedel, Wichita, KS (US)

(72) Inventor: David R Riedel, Wichita, KS (US)

(73) Assignee: David R. Riedel, Wichita, KS (US)

( * ) Notice: Subject to any disclaimer, the term of this patent is extended or adjusted under 35 U.S.C. 154(b) by 679 days.

(21) Appl. No.: 16/816,909

(22) Filed: Mar. 12, 2020

(65) Prior Publication Data

US 2020/0206022 A1    Jul. 2, 2020

(51) Int. Cl.
*A61F 7/00* (2006.01)
*A61F 7/02* (2006.01)

(52) U.S. Cl.
CPC ........ *A61F 7/00* (2013.01); *A61F 2007/0028* (2013.01); *A61F 2007/0067* (2013.01); *A61F 2007/0236* (2013.01)

(58) Field of Classification Search
CPC ...... A61F 2007/0067; A61F 2007/0068; A61F 2007/0028; A61F 2007/0048; F04D 25/0084; F04D 25/0086; A41D 13/0025; A41D 13/0056
See application file for complete search history.

(56) References Cited

U.S. PATENT DOCUMENTS

| | | | |
|---|---|---|---|
| 5,564,124 A * | 10/1996 | Elsherif | A41D 13/0025 2/457 |
| 7,124,593 B2 | 10/2006 | Feher | |
| 8,302,421 B2 | 11/2012 | Korytnikov | |
| 9,851,113 B2 | 12/2017 | Clemente | |
| 10,426,204 B2 | 10/2019 | Squires et al. | |
| 2007/0118956 A1 * | 5/2007 | Sawicki | A41D 13/0025 2/69 |
| 2007/0190923 A1 | 8/2007 | Gilley et al. | |
| 2012/0031582 A1 | 2/2012 | Sullivan | |
| 2014/0093404 A1 | 4/2014 | Long | |
| 2016/0327290 A1 * | 11/2016 | Clemente | A41D 13/0056 |
| 2018/0094838 A1 | 4/2018 | Ichiki et al. | |
| 2018/0220721 A1 | 9/2018 | Houde | |

FOREIGN PATENT DOCUMENTS

| | | |
|---|---|---|
| DE | 20201400825 | 10/2014 |
| KR | 200377844 | 3/2005 |
| KR | 100498113 B1 | 7/2005 |

(Continued)

*Primary Examiner* — Kaitlyn E Smith
(74) *Attorney, Agent, or Firm* — Kenneth H. Jack; Davis & Jack, L.L.C.

(57) ABSTRACT

An assembly for gluteal cleft moisture reduction including a case having a plurality of walls, the case being opened by an air input port; an air tube having upper and lower ends wherein the tube's upper end forms a dorsal extension communicating with an opening in the flexible skin contact plate mounted on the case, the plate ventrally overlying the air tube; an air conduit housed within the case, the conduit having input and output ends communicating with the case's air input port and with the air tube; an electric motor and air impeller combination housed within the case, the combination being adapted for moving air through the air conduit; an electric battery within the case; and a matrix of electric conductors operatively interconnecting the electric motor and the electric battery.

15 Claims, 5 Drawing Sheets

(56) References Cited

FOREIGN PATENT DOCUMENTS

| | | |
|---|---|---|
| KR | 20060081315 | 7/2006 |
| KR | 20080095506 | 10/2008 |
| KR | 20110000357 | 1/2011 |
| KR | 101217530 B1 | 1/2013 |
| KR | 101713497 | 3/2017 |
| SE | 425347 | 9/1982 |

* cited by examiner

ASSEMBLY FOR GLUTEAL CLEFT MOISTURE REDUCTION

FIELD OF THE INVENTION

This invention relates to apparatus and assemblies for reducing sweat and body moisture. More particularly, this invention relates to such apparatus which are specially adapted for absorbently collecting such moisture and for directing flows of moisture drying air beneath a user's garments.

BACKGROUND OF THE INVENTION

Persons who suffer from external anal hemorrhoids and who are required to perform work in hot outdoor environments often experience sweat induced hemorrhoidal irritation. During such hot work, sweat emanating at the worker's lower back and coccyx area may commonly flow downwardly and along the hemorrhoid sufferer's gluteal cleft area, causing painful irritation due to the salinity of the sweat. Such flows and accumulations of sweat may, on occasion, induce anal irritation where the worker is not a hemorrhoid sufferer.

The instant inventive assembly for gluteal cleft moisture reduction solves or ameliorates such gluteal cleft area irritation effects by providing a specialized battery and electric motor powered air driving device which is further capable of absorbing sweat within and above a user's gluteal cleft area. The absorption and sweat drying functions of the instant invention advantageously prevent or reduce the incidence of anal and/or hemorrhoidal sweat induced irritation.

BRIEF SUMMARY OF THE INVENTION

A first structural component of the instant inventive assembly for gluteal cleft moisture reduction comprises a case or housing having a plurality of walls. In the preferred embodiment, the case comprises a small laterally oblongated plastic box. Also, in the preferred embodiment, the case is opened by a rearwardly or dorsally opening air input port, and by a frontwardly or ventrally opening air output port.

A further structural component of the instant inventive assembly comprises an air tube having upper and lower ends. In the preferred embodiment, such tube is composed of durable flexible plastic, and the upper end of such tube forms a dorsal or rearward extension. In the preferred embodiment, such dorsal extension is attached in communication with the case's air output port and in communication with an output end of an internal air conduit.

The instant inventive assembly further comprises a flexible skin contact plate which is preferably mounted to the case so that frontward portions of the plate ventrally overlie a medial portion of the air tube. The flexible skin contact plate is preferably composed of durable flexible plastic sheeting and is substantially rectangularly configured. Suitably, such plate may be alternatively composed of leather. In the preferred embodiment, an upper end of the flexible skin contact plate forms an upwardly and rearwardly arching extension whose distal end forms a downward extension. In the preferred embodiment, the rearwardly or dorsally facing surface of the plate's downward extension serves as an attachment land for adhesive mounting of the contact plate upon a forward or ventral wall of the case. The plate, the arching dorsal extension, and the downward extension together advantageously form a waistband engaging "U" hook.

A further structural component of the instant inventive assembly comprises an air conduit which is mounted and housed within the case. Such conduit preferably presents input and output ends which respectively communicate with the case's air input port and with the input end of the air's dorsal extension, such air input end coinciding with the case's air output port. While provision of a separate conduit housed within the case is preferred, the conduit component may suitably comprise the interior space of the case itself.

A further structural component of the instant inventive assembly comprises an electric motor and air impeller or fan combination which is mounted and housed within the case. Such combination is preferably situated relative to the conduit in a manner allowing rotary operation of the impeller to drive air through the conduit from the case's intake port to the upper end of the air tube.

A further structural component of the instant inventive assembly comprises an electric battery which is mounted and housed within the case. In a preferred embodiment, the electric battery is rechargeable.

A further structural component of the instant inventive assembly comprises a matrix or network of electrical conductors which operatively electrically interconnects the electric motor and the electric battery.

In use of the instant inventive assembly, a user may situate the flexible skin contact plate between the user's undershorts and gluteus maximus and gluteal cleft area. Upon so situating the flexible skin contact plate, the air tube directly dorsally overlies the dorsal face of the skin contact plate, and in such usage configuration, the case typically resides immediately outside of the user's pants at the user's waistline or beltline. In such use configuration, the dorsal extensions of the upper end of the air tube and the upper end of the skin contact plate advantageously form a "U" shaped hooking and mounting structure which suspends the case, the air tube, and the skin contact plate at the user's beltline. In the preferred embodiment, the throat of the "U" hook is laterally co-extensive with the lateral dimension of the ventral end of the case.

Upon such installation of the inventive assembly, and upon actuating the electric motor and air impeller, air is advantageously drawn into the case's intake port to flow through the conduit, and to exit at the case's air output port. Thence, the air is conducted by the air tube downwardly and typically arcuately forwardly along the user's gluteal cleft area, advantageously injecting sweat drying air into and along such area. Forced air drying performed by the instant inventive assembly at such anatomical areas advantageously reduces sweat induced hemorrhoidal irritation.

In a preferred embodiment, the instant inventive assembly further comprises an absorbent fabric boot, suitably comprising cotton terrycloth, whose periphery is fitted to engage the periphery of the ventral aspect of the skin contact plate. Such boot may advantageously absorb sweat flowing downwardly from the small of the user's back, beneficially reducing the volume of moisture required to be dried by the air flow emitting from the air tube.

Accordingly, objects of the instant invention include the provision of an assembly for gluteal cleft aeration which incorporates structures, as described above, and which arranges those structures in manners described above, for the performance of beneficial functions described above.

Other and further objects, benefits, and advantages of the instant invention will become known to those skilled in the art upon review of the Detailed Description which follows, and upon review of the appended drawings.

DETAILED DESCRIPTION OF A PREFERRED EMBODIMENT

Figure 1:
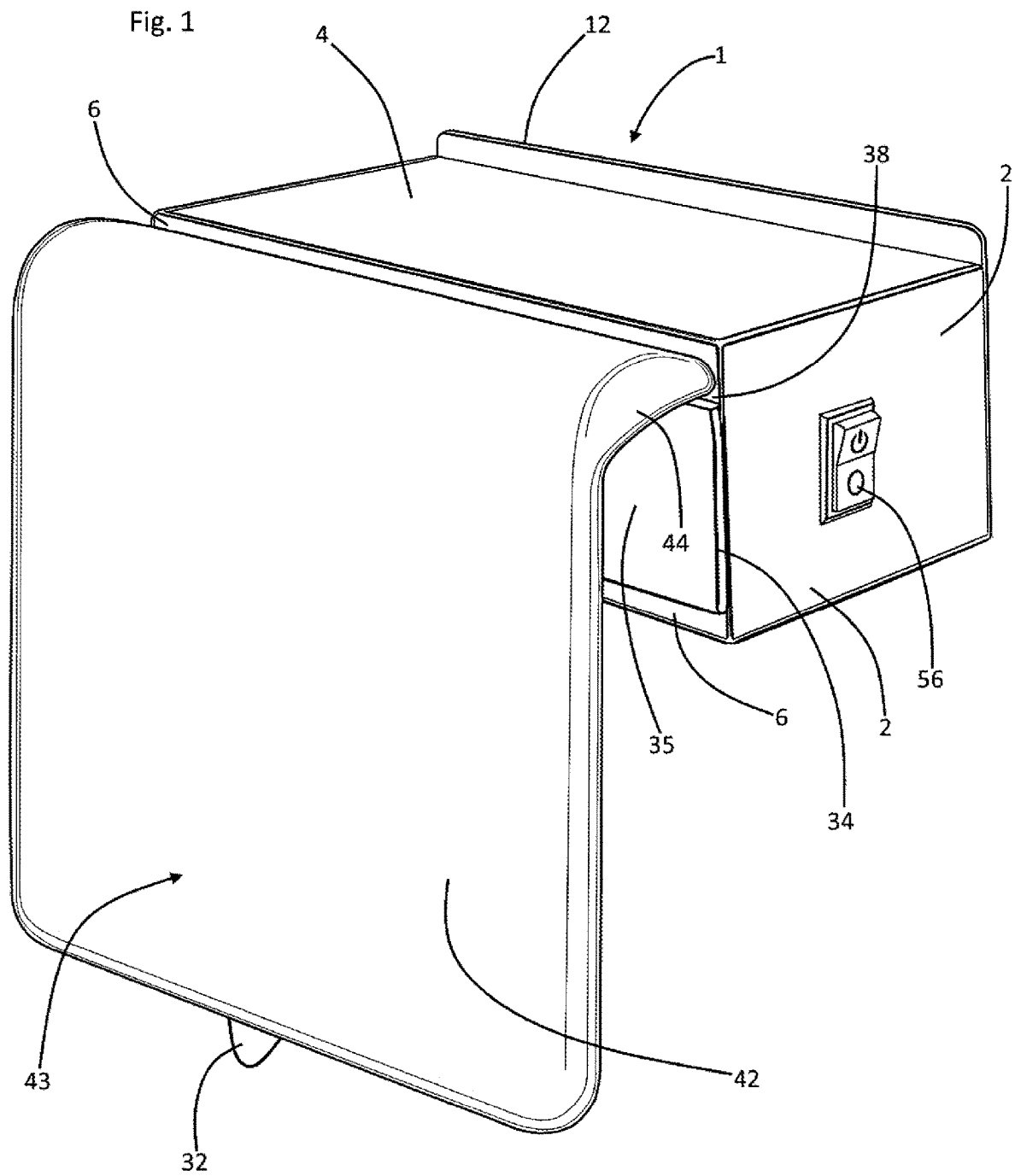
FIG. 1 is a perspective view of the instant inventive assembly for gluteal cleft moisture reduction.

Referring now to the drawings, and in particular to Drawing FIG. 1, a preferred embodiment of the instant inventive assembly for gluteal cleft moisture reduction is referred to generally by Reference Arrow 1. The assembly 1 includes a case or housing element which, referring further to FIGS. 3 and 5, includes an upper wall or ceiling 4, a right wall 2, a left wall 3, a forward or ventral wall 6, and rearward or dorsal wall segments 8 and 17. In a preferred embodiment, the case component is composed of durable injection molded plastic.

In a preferred embodiment, the case's smaller rear wall segment or section 17 includes a screened air inlet port 16, and such wall 17 and port 16 are forwardly canted or angled in order to form an air inflow clearance space 14, such space being leftwardly bounded by wall 18. The inflow clearance space 14 formed by walls 17 and 18 advantageously allows a user's shirttail to dorsally overlie the case without blocking or obstructing the screened intake port 16. A shirttail retaining flange 12 preferably extends upwardly from the rear or dorsal end of the upper wall or ceiling 4, such flange 12 allowing the shirttail to alternatively rest upon ceiling 4 without falling rearwardly over the rear wall segments 8 and 17.

Figure 5:
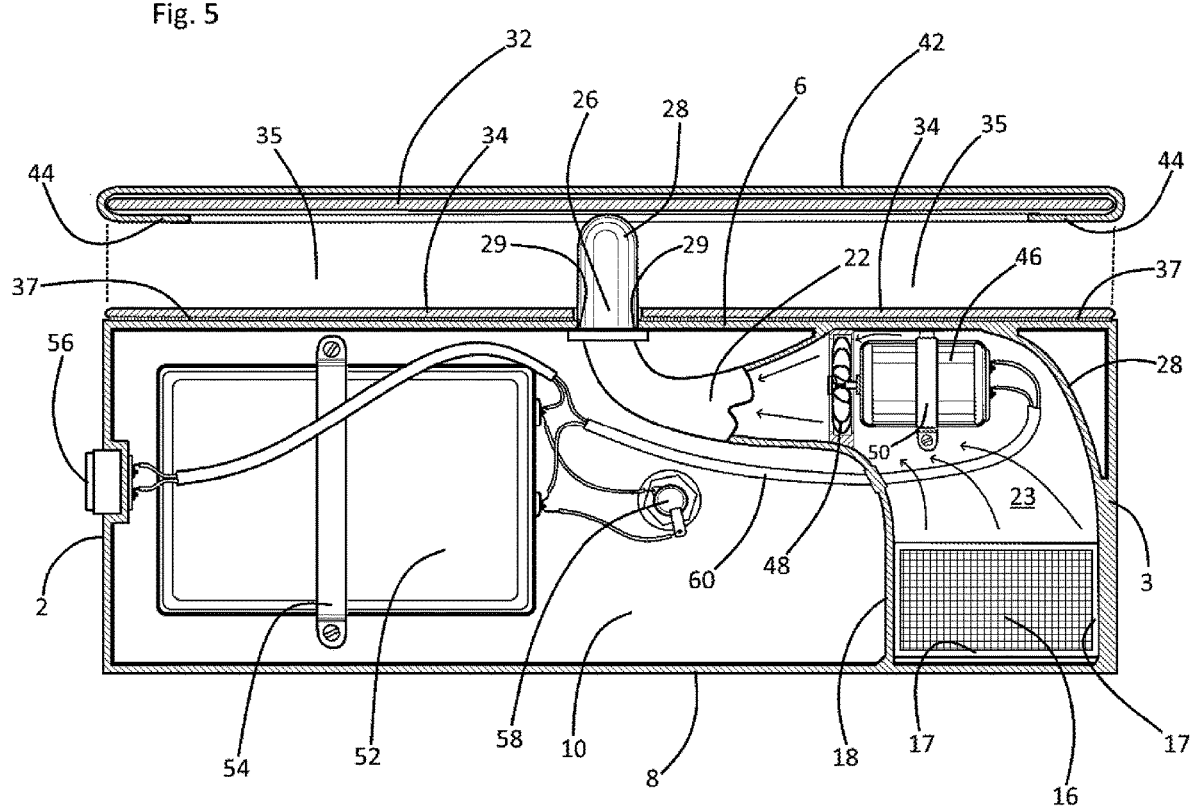
FIG. 5 is a sectional view as indicated in FIG. 4.

As shown in FIG. 5, an internal air flow directing conduit 22 including air guiding walls 18 and 28 spans between and interconnects the air inlet port 16 with an air outlet port 29, such port 29 opening the case at the front wall 6. Suitably, the conduit 22 may alternatively comprise the interior of the case.

A flexible plastic air tube 33 having an upper end 28 and a lower air outlet end 32 is preferably supported and positioned immediately ventrally from the ventral or front wall 6 of the case. In the preferred embodiment, a dorsal tube extension 26 cantilevers rearwardly from the upper end 28 of the air tube 33, such extension 26 passing through or communicating with the case's air outlet port 29. In the preferred embodiment, the extension 26 communicates with the outlet end of the conduit 22 at the wall port 29.

Figure 2:
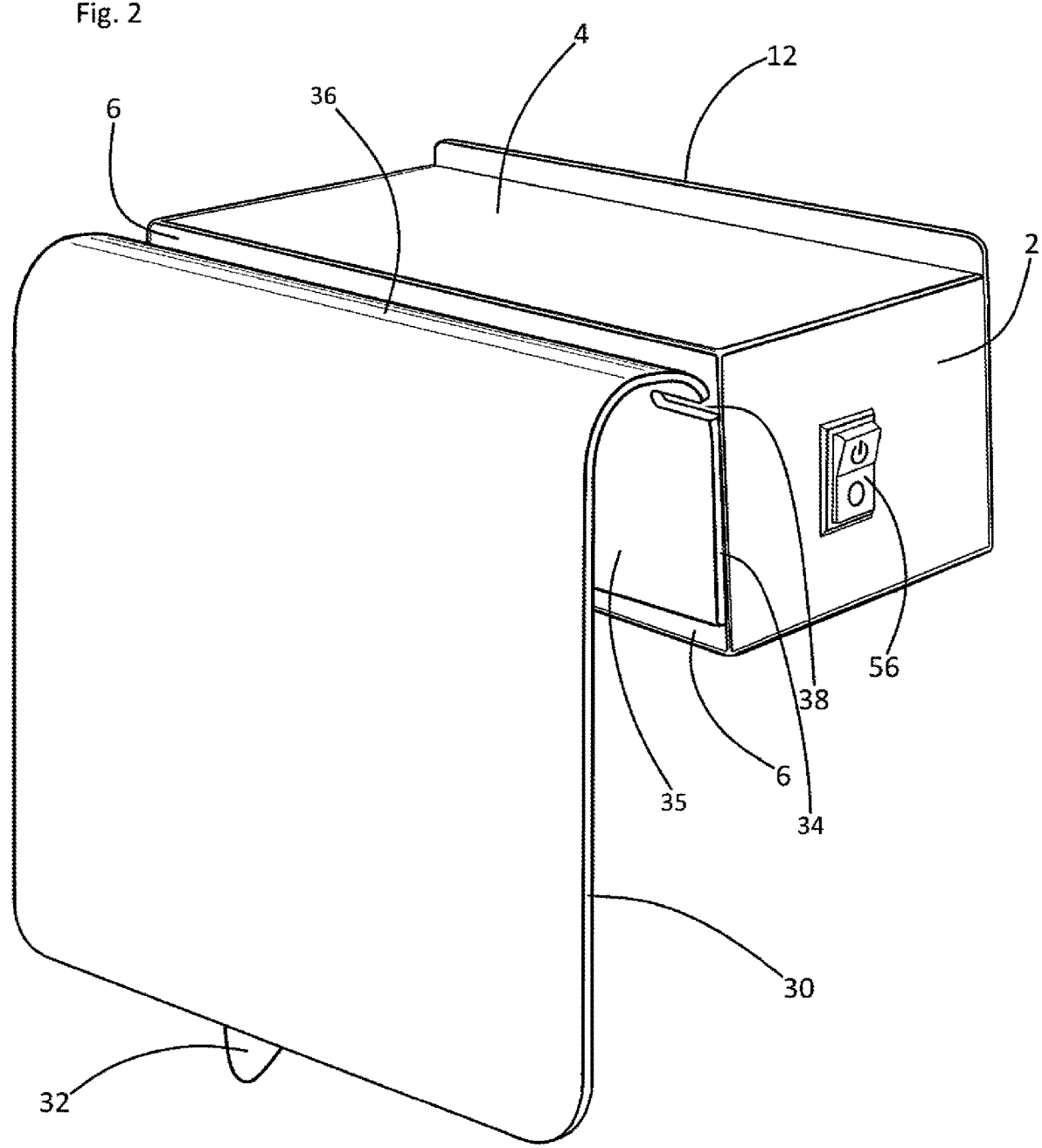
FIG. 2 redepicts the structure of FIG. 1, the view of FIG. 2 showing an absorbent fabric boot component removed.
Figure 3:
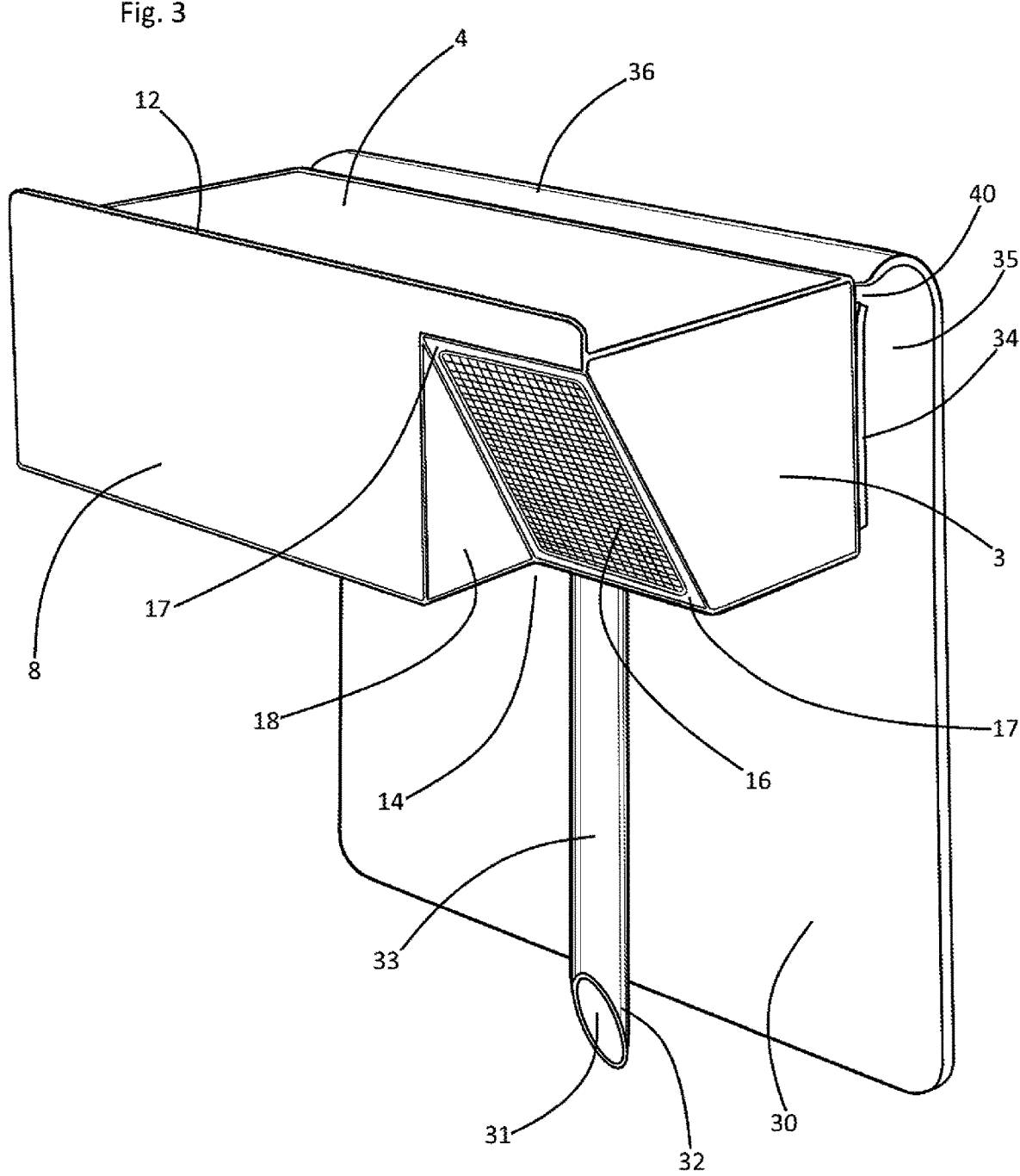
FIG. 3 is a reverse perspective view of the structure of FIG. 2.

Referring simultaneously to FIGS. 2, 3, and 5, a skin contact plate 30 is provided, such plate preferably being composed of durable and flexible plastic. In the preferred embodiment, a ventral or frontward portion of the plate 30 is substantially square or rectangular, such plate having an arcuately curved dorsal extension 36 at its upper end. A downward extension 34 portion of the plate is preferably formed wholly with the distal end of the dorsal extension 36, such downward extension 34 advantageously providing a dorsally facing surface for adhesive mounting upon the front or ventral face of the case's front wall 6. As shown in FIG. 5, a layer of durable adhesive 37 bonds the downward extension 34 to the outer surface of such wall.

As indicated in FIGS. 2 and 3, the upper end of the skin contact plate 30 forms a downwardly opening "U" structure 35 which may advantageously hook against a user's pants waistline for suspending and positioning the case, the air tube 33 and the skin contact plate 30 at the small of the user's back. The pants engaging throat which is formed by such "U" hook preferably extends along the full lateral width of the case.

Figure 4:
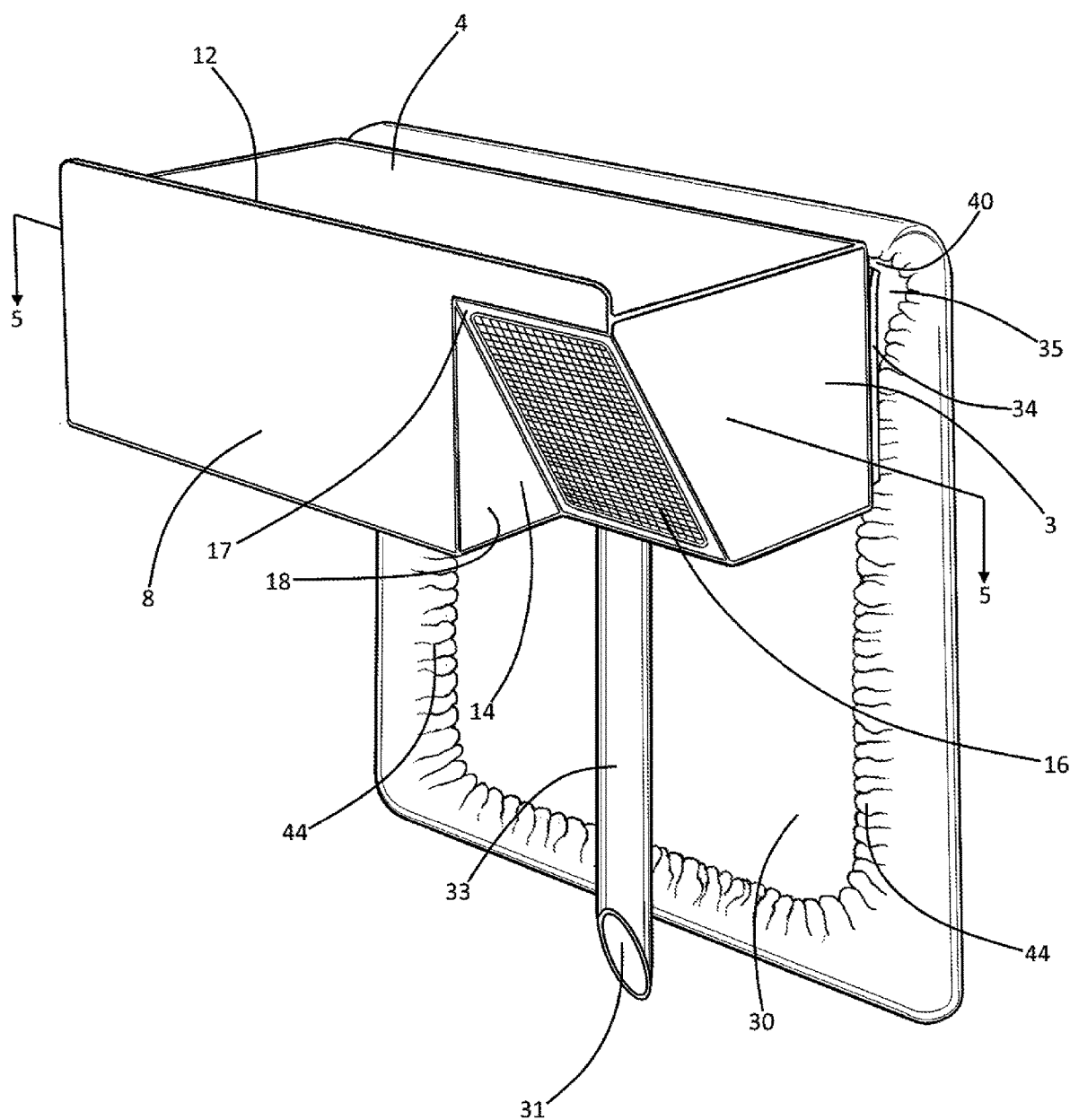
FIG. 4 redepicts the view of FIG. 3, the view of FIG. 4 showing the boot element of FIG. 1 reattached.

In the preferred embodiment, as shown in FIGS. 1 and 4, left and right fabric boot receiving and retaining slots 38 and 40 are formed at the distal end of extension 36. Such slots 38 and 40 advantageously receive an elastic peripheral edge 44 of a moisture absorbing fabric boot 43.

Referring to FIG. 5, a DC electric motor 46 and impeller 48 combination is secured via mounting bracket 50 within the interior 23 of the conduit 22. Powered operation of such motor 46 and fan 48 draws air through screened port 16 into the interior 23 of conduit 22, such flow being in the direction of drawn arrows. The fan drawn air exits at port 29 in communication with the dorsal extension 26 at the upper end 28 of air tube 33. Such air then passes downwardly through the bore 31 of tube 33 to exit at the tube's lower end 32.

In order to power the electric motor 46, a rechargeable battery 52 is preferably provided, such battery being mounted by bracket 54 within the interior of the case. In the preferred embodiment, an on/off circuit breaking electrical switch 56 is mounted upon a lateral wall 2 for actuating and deactuating the motor 46. A network of wire conductors 60 preferably operatively electrically interconnects the switch 56, the battery 52, and the motor 46. Where the battery 52 is rechargeable, as is preferred, a female charging plug socket 58 is preferably further incorporated within the assembly's electric circuitry. Such charging socket 58 is preferably mounted upon the floor or lower wall 10 of the case, such downward positioning of the socket 58 advantageously protecting against entry of moisture into the socket.

In operation, the instant inventive assembly may be initially configured as indicated in Drawing FIGS. 1, 4, and 5, with the fabric boot 43 covering the skin contact plate 30. To accomplish such initial configuration, the boot's elastic hem 44 may be manually guided into engagements with the left and right boot retention slots 38 and 40, such engagements advantageously locking the boot 43 in place. The forward face 42 of the fabric boot 43 may be advantageously composed of an absorbent fabric, such as cotton terrycloth, for enhanced sweat absorption.

Thereafter, the boot 43, the plate 30, and the air tube 33 may be simultaneously downwardly inserted as a single unit along the small of the user's back. Such insertion step preferably situates those structures between the user's lower back and buttocks and the waistline of the user's underpants. Upon such placement of the inventive assembly, the "U" hook character of the upper end of skin contact plate engages the waistline of the user's pants (not depicted within views), advantageously suspending all structures of the assembly therefrom.

Thereafter, the on/off switch 56 may be manually moved to its "on" position, actuating fan 48 and causing air drawn through port 16 to emit at the lower end 32 of the air tube 33. Such emitted air flows along and over the user's gluteal cleft area, advantageously assisting in drying of sweat within such area. The moisture drying effect of the emitted air works in a complimentary fashion with the sweat absorbing action of the boot 43.

While the principles of the invention have been made clear in the above illustrative embodiment, those skilled in the art may make modifications to the structure, arrangement, portions and components of the invention without departing from those principles. Accordingly, it is intended that the description and drawings be interpreted as illustrative and not in the limiting sense, and that the invention be given a scope commensurate with the appended claims.

The invention hereby claimed is:

1. An assembly for gluteal cleft moisture reduction comprising:
   (a) a case having a plurality of walls, the case being opened by an air input port, the case having a ventral end;
   (b) an air tube having an upper end, a lower end, and a medial portion spanning between said ends, said tube extending downwardly from and ventrally overlying the case's ventral end;
   (c) a downwardly opening "U" hook having a ventral arm, said arm comprising a flexible skin contact plate ventrally overlying the air tube's medial portion;
   (d) an air conduit within the case, said conduit having an input end communicating with the case's air input port and having an output end communicating with the air tube's upper end;
   (e) an electric motor and air impeller combination within the case, said combination being adapted for moving air through the air conduit;
   (f) an electric battery within the case; and
   (g) a matrix of electrical conductors operatively interconnecting the electric motor and the electric battery.

2. The assembly for gluteal cleft moisture reduction of claim 1 further comprising a fabric boot covering the flexible skin contact plate.

3. The assembly for gluteal cleft moisture reduction of claim 2 further comprising an on/off switch and a recharging socket, said switch and said socket being operatively incorporated within the matrix of electrical conductors.

4. The assembly for gluteal cleft moisture reduction of claim 3 wherein the on/off switch is supported upon a lateral case wall.

5. The assembly for gluteal cleft moisture reduction of claim 4 wherein the recharging socket is supported upon a lower case wall.

6. An assembly for gluteal cleft moisture reduction comprising:
   (a) a case having a plurality of walls, the case being opened by an air input port, the case having a ventral end;
   (b) an air tube having an upper end, a lower end, and a medial portion spanning between said ends, said tube extending downwardly from the case's ventral end;
   (c) a flexible skin contact plate ventrally overlying the air tube's medial portion;
   (d) fabric boot covering the flexible skin contact plate;
   (e) an air conduit within the case, said conduit having an input end communicating with the case's air input port and having an output end communicating with the air tube's upper end;
   (f) an electric motor and air impeller combination within the case, said combination being adapted for moving air through the air conduit;
   (g) an electric battery within the case; and
   (h) a matrix of electrical conductors operatively interconnecting the electric motor and the electric battery; and
   (i) a dorsal extension having a dorsal end, said extension being formed wholly with an upper end of the flexible skin contact plate.

7. The assembly for gluteal cleft moisture reduction of claim 6 further comprising a downward extension formed wholly with the dorsal end of the dorsal extension, said downward extension being fixedly attached to the ventral end of the case.

8. The assembly for gluteal cleft moisture reduction of claim 7 wherein the flexible skin contact plate, the second extension, and the downward extension form a downwardly opening "U" hook.

9. The assembly for gluteal cleft moisture reduction of claim 8 wherein the "U" hook forms a laterally extending waistband receiving throat, wherein the case has a lateral dimension, and wherein said throat's lateral extension is substantially equal to the case's lateral dimension.

10. The assembly for gluteal cleft moisture reduction of claim 7 wherein the flexible skin contact plate has a peripheral edge, and wherein the boot comprises an elastic peripheral hem adapted for engaging said peripheral edge.

11. The assembly for gluteal cleft moisture reduction of claim 10 wherein the air tube comprises flexible plastic.

12. The assembly for gluteal cleft moisture reduction of claim 11 wherein the plurality of walls comprises a ceiling having a dorsal end, and further comprising a shirttail engaging flange fixedly attached to and extending upwardly from said dorsal end.

13. The assembly for gluteal cleft moisture reduction of claim 11 wherein the plurality of walls comprises a segmented dorsal wall, wherein one of said dorsal wall's segments is displaced ventrally with respect to another of said dorsal wall's segments, and wherein the one of the dorsal wall's segments ventrally bounds a shirttail clearance space.

14. The assembly for gluteal cleft moisture reduction of claim 13 further comprising a screen covering the case's air input port.

15. The assembly for gluteal cleft moisture reduction of claim 14 wherein the battery is rechargeable.

* * * * *